(12) United States Patent
Kohashi et al.

(10) Patent No.: US 11,170,972 B2
(45) Date of Patent: Nov. 9, 2021

(54) SCANNING ELECTRON MICROSCOPE AND METHOD FOR ANALYZING SECONDARY ELECTRON SPIN POLARIZATION

(71) Applicant: Hitachi High-Tech Corporation, Tokyo (JP)

(72) Inventors: Teruo Kohashi, Tokyo (JP); Hideo Morishita, Tokyo (JP); Junichi Katane, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 0 days.

(21) Appl. No.: 16/979,263

(22) PCT Filed: Mar. 27, 2018

(86) PCT No.: PCT/JP2018/012592
§ 371 (c)(1),
(2) Date: Sep. 9, 2020

(87) PCT Pub. No.: WO2019/186736
PCT Pub. Date: Oct. 3, 2019

(65) Prior Publication Data
US 2020/0402762 A1    Dec. 24, 2020

(51) Int. Cl.
*H01J 37/28* (2006.01)
*H01J 37/20* (2006.01)
*H01J 37/244* (2006.01)

(52) U.S. Cl.
CPC .............. *H01J 37/28* (2013.01); *H01J 37/20* (2013.01); *H01J 37/244* (2013.01); *H01J 2237/24557* (2013.01)

(58) Field of Classification Search
CPC .. H01J 37/00; H01J 37/02; H01J 37/28; H01J 37/20; H01J 37/244; H01J 37/268;
(Continued)

(56) References Cited

U.S. PATENT DOCUMENTS

2010/0155598 A1* 6/2010 Kohashi ............... G01R 33/093
250/311

FOREIGN PATENT DOCUMENTS

JP          20103450 A        1/2010
JP        2010151455 A        7/2010
(Continued)

OTHER PUBLICATIONS

Search Report dated Jun. 19, 2018 in International Application No. PCT/JP2018/012592.
(Continued)

*Primary Examiner* — Jason L McCormack
(74) *Attorney, Agent, or Firm* — Miles & Stockbridge, P.C.

(57) ABSTRACT

A scanning electron microscope includes a spin detector configured to measure spin polarization of a secondary electron emitted from a sample, and an analysis device configured to analyze measurement data of the spin detector. The analysis device determines a width of a region where the secondary electron spin polarization locally changes in the measurement data. The analysis device further evaluates a strain in the sample based on the width of the region. With a configuration of the scanning electron microscope, it is possible to perform analysis of a strain in a magnetic material with high accuracy.

15 Claims, 9 Drawing Sheets

(58) Field of Classification Search
CPC ........ H01J 2237/24557; G01N 33/204; G01N 33/2251; G01N 2223/624; G01N 2223/607; G01N 2223/24585
USPC .......................................... 250/306, 307, 311
See application file for complete search history.

(56) References Cited

FOREIGN PATENT DOCUMENTS

| | | |
|---|---|---|
| JP | 2011059057 A | 3/2011 |
| JP | 2014127224 A | 7/2014 |

OTHER PUBLICATIONS

Written Opinion dated Jun. 19, 2018 in International Application No. PCT/JP2018/012592.

* cited by examiner

[FIG. 1A]
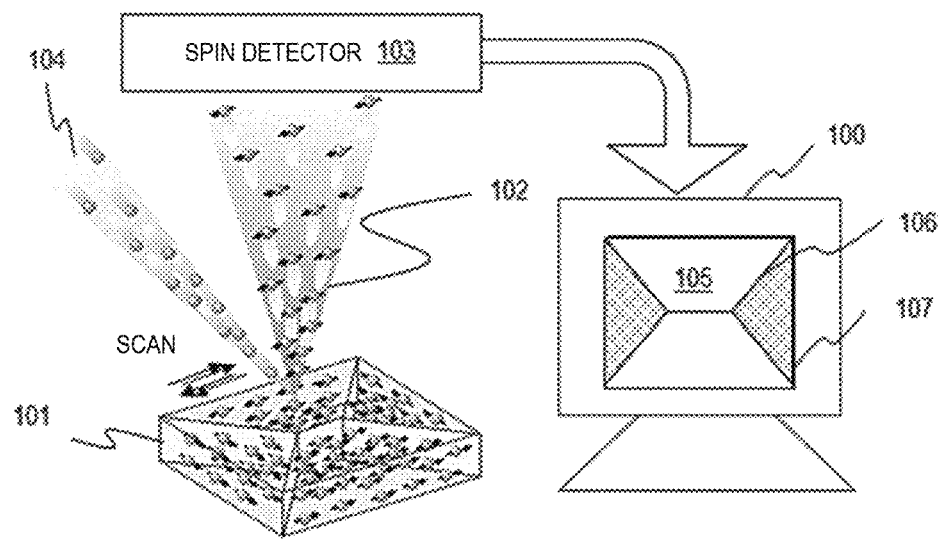
[FIG. 1B]
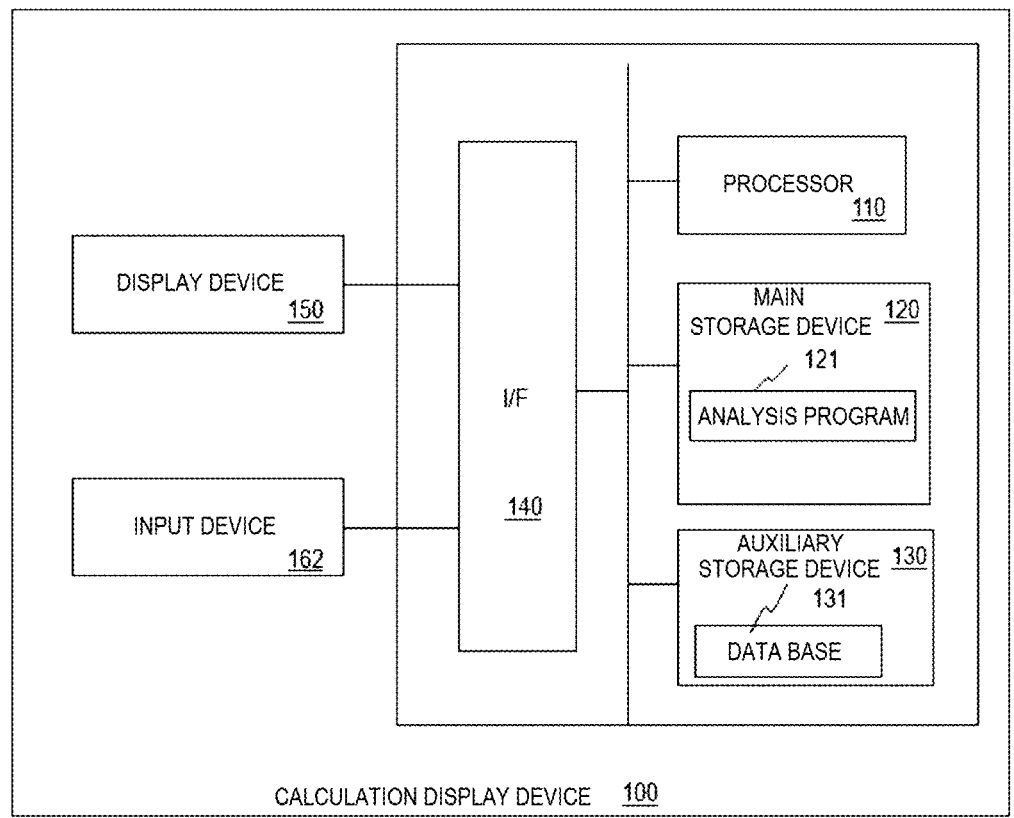

[FIG. 2A]
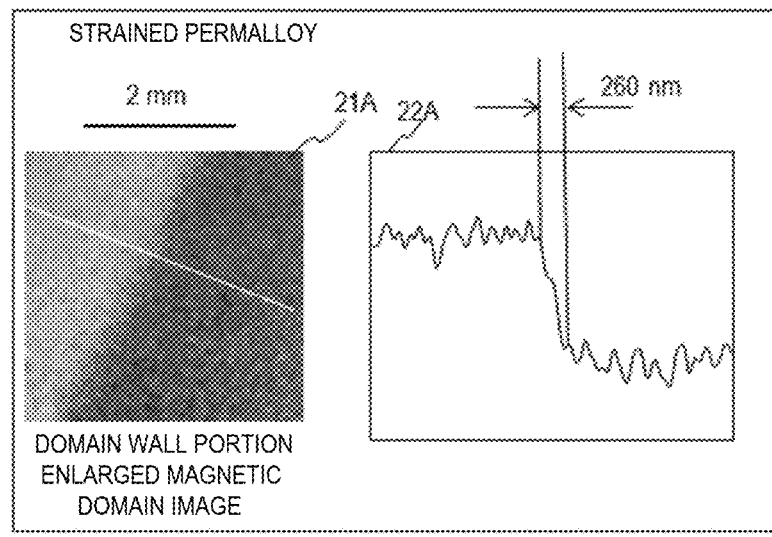
[FIG. 2B]
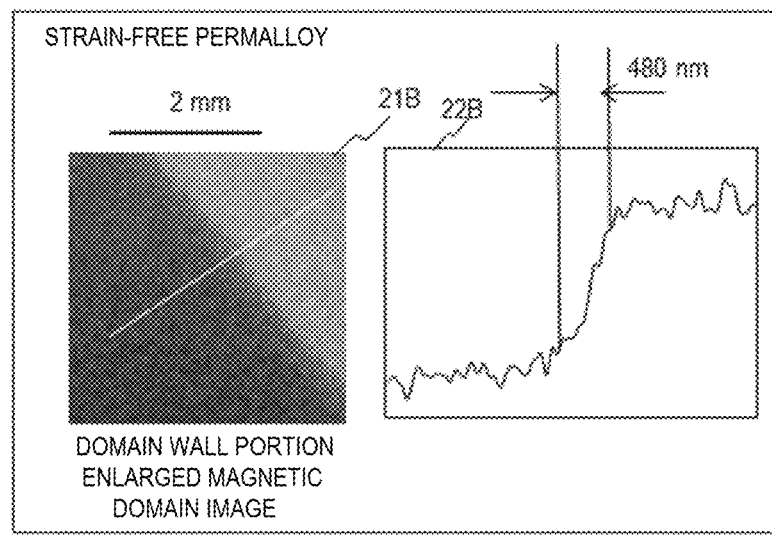

[FIG. 3]
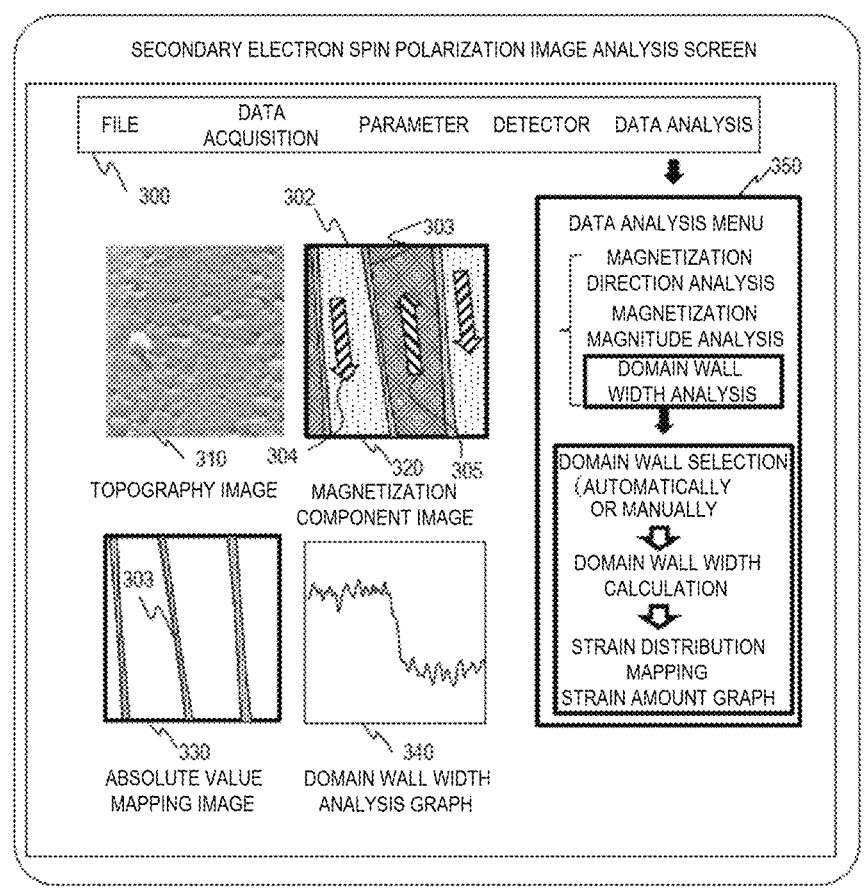

[FIG. 4A]
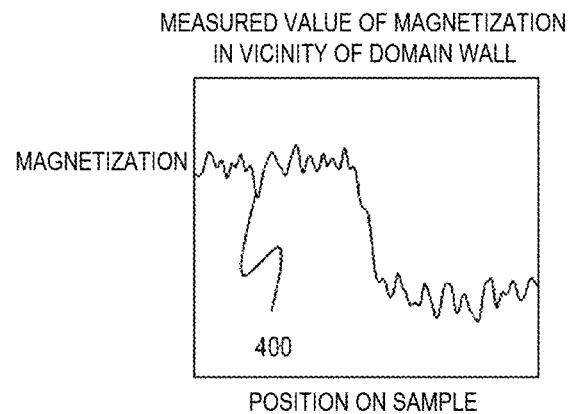
[FIG. 4B]
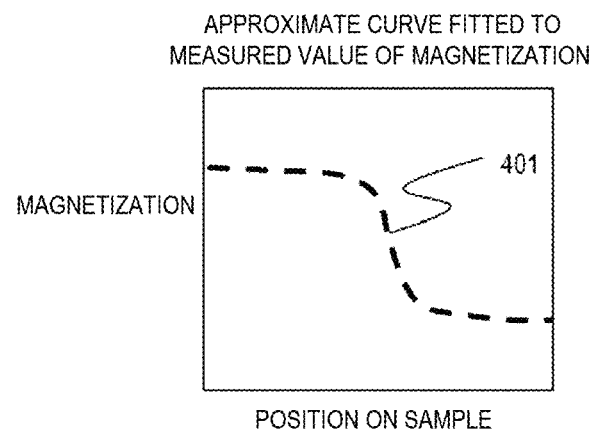
[FIG. 4C]
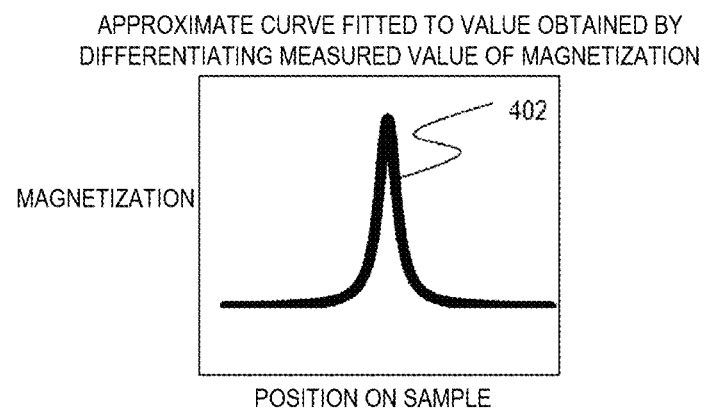

[FIG. 5A]
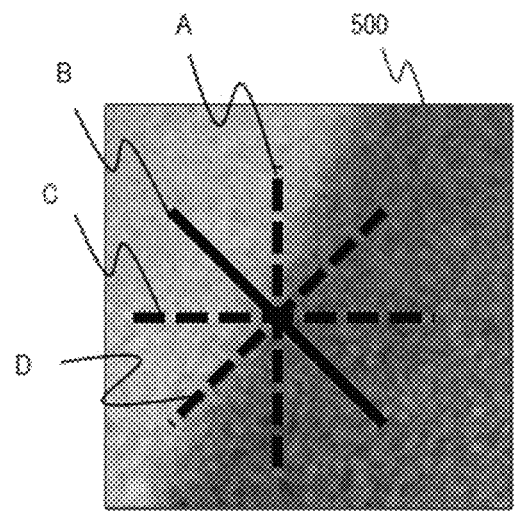
[FIG. 5B]
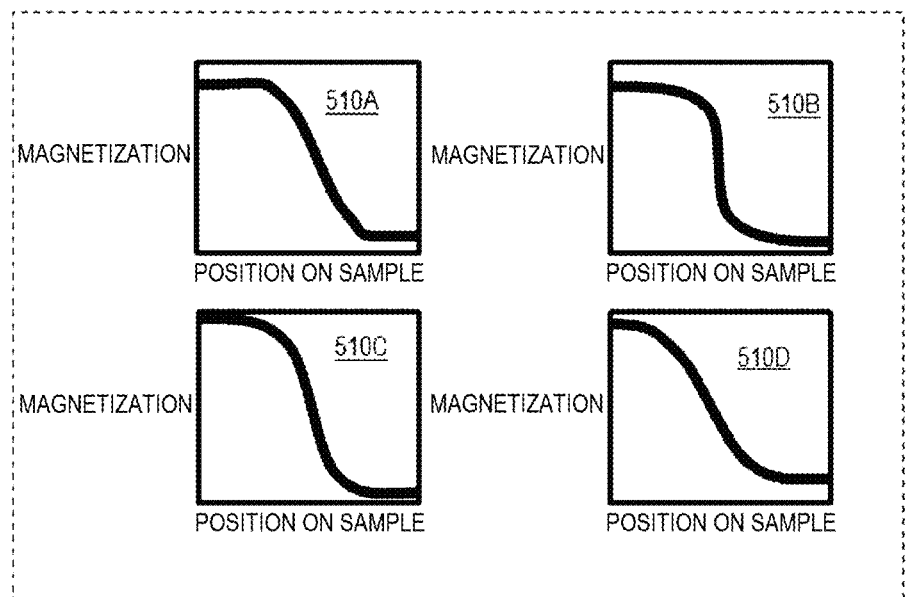

[FIG. 6A]
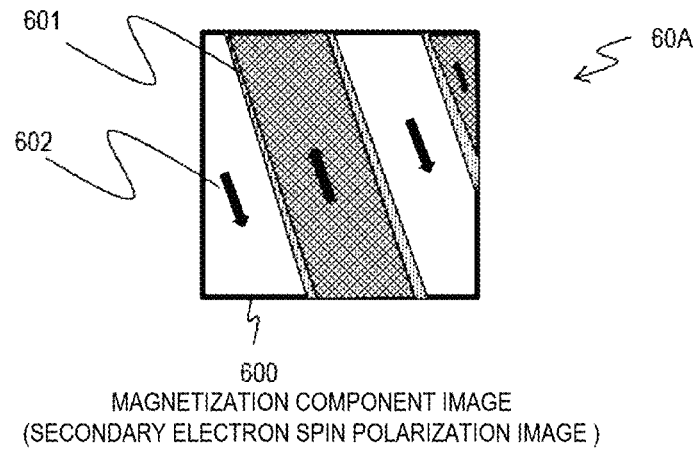
MAGNETIZATION COMPONENT IMAGE
(SECONDARY ELECTRON SPIN POLARIZATION IMAGE)
[FIG. 6B]
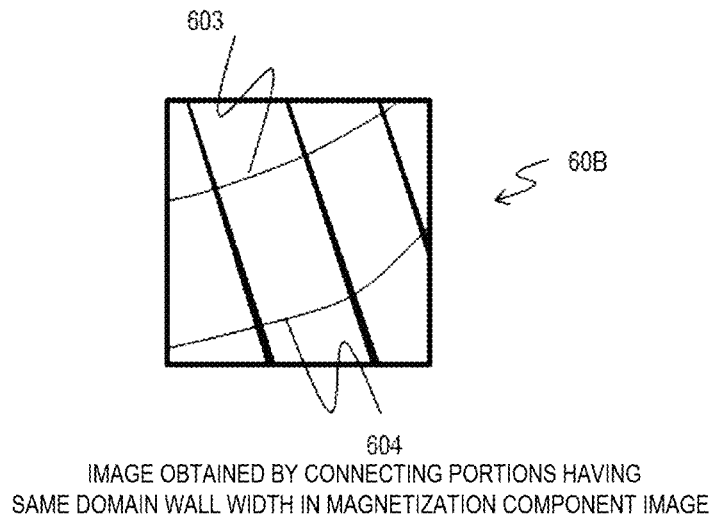
IMAGE OBTAINED BY CONNECTING PORTIONS HAVING
SAME DOMAIN WALL WIDTH IN MAGNETIZATION COMPONENT IMAGE
[FIG. 6C]
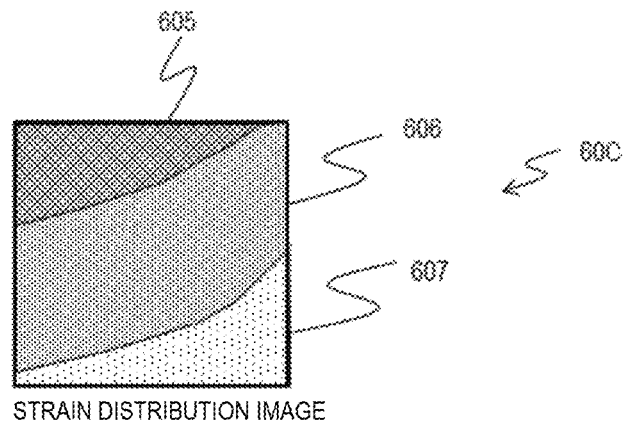
STRAIN DISTRIBUTION IMAGE

[FIG. 7]
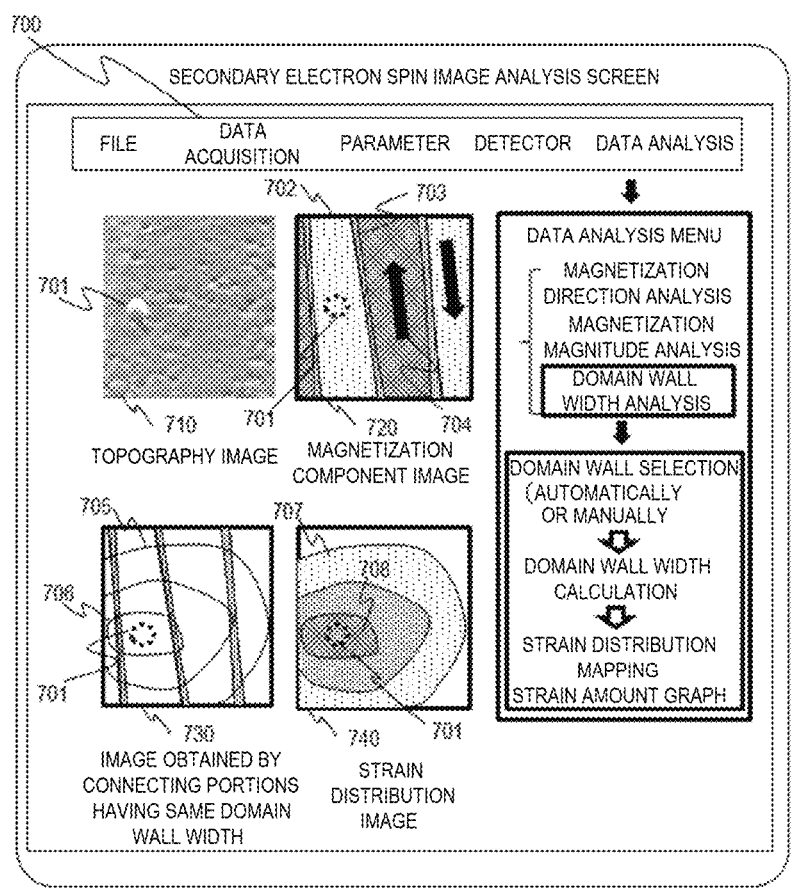

[FIG. 8A]
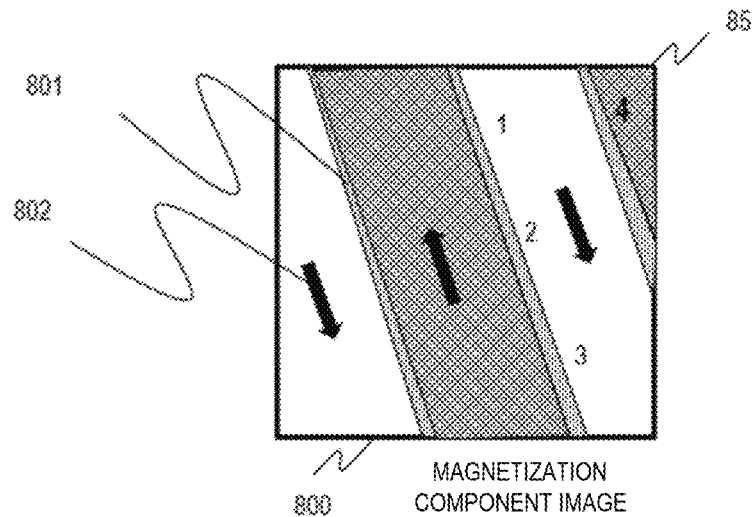
MAGNETIZATION COMPONENT IMAGE
[FIG. 8B]
| DOMAIN WALL POSITION No. | DOMAIN WALL WIDTH | ANGLE BETWEEN DOMAIN WALL AND MAGNETIZATION | STRAIN AMOUNT |
|---|---|---|---|
| 1 | 180 | 5 | 0.0030% |
| 2 | 200 | 15 | 0.0025% |
| 3 | 270 | 20 | 0.0005% |
| 4 | 150 | 15 | 0.0040% |
| AVERAGE | 170 | 173.75 | 0.0025% |
| DISPERSION | 88.3171 | 15.4784797 | 0.0015% |
DOMAIN WALL ANALYSIS RESULT

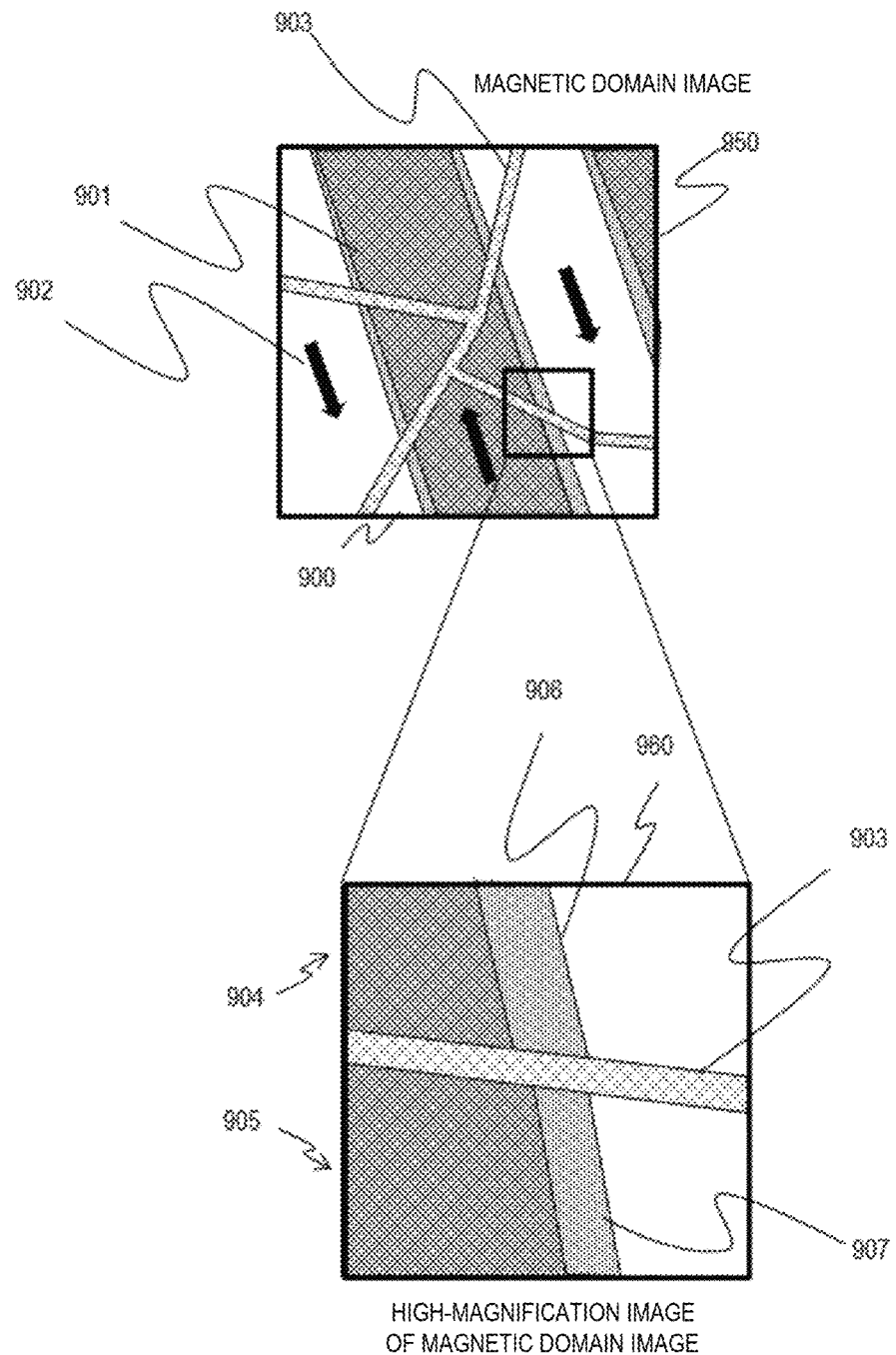
[FIG. 9]
MAGNETIC DOMAIN IMAGE
HIGH-MAGNIFICATION IMAGE
OF MAGNETIC DOMAIN IMAGE

SCANNING ELECTRON MICROSCOPE AND METHOD FOR ANALYZING SECONDARY ELECTRON SPIN POLARIZATION

TECHNICAL FIELD

The present disclosure relates to a scanning electron microscope and a method for analyzing secondary electron spin polarization.

BACKGROUND ART

There is a method of detecting spin polarization of secondary electrons from a magnetic material which is a sample and performing magnetization mapping in a scanning electron microscope (for example, see PTL1). It is known that an origin of the magnetization is the spin polarization of the electrons inside the material and the spin polarization is almost maintained even when the electrons are emitted as the secondary electrons out of the sample.

Therefore, the magnetization at a secondary electron emission point can be evaluated by transporting the secondary electrons to a spin detector and measuring the spin polarization. Further, when a surface of the sample is scanned with a primary electron beam and the spin polarization of the secondary electrons is sequentially measured, the magnetization mapping within a scanning range is possible. The method is known as a spin-polarized scanning electron microscope (spin SEM) and has advantages such as high resolution at a level of 10 nm and three-dimensional detection of all magnetization directions. In the above description, the method has been used in a field of basic magnetism and evaluation of a magnetic device such as a magnetic recording material and a permanent magnet material.

CITATION LIST

Patent Literature

PTL 1: JP-A-2011-059057

SUMMARY OF INVENTION

Technical Problem

It is known that a strain existing in a material has a great influence on properties of a steel material and a magnet material. For example, the strain is a cause of deterioration in a structural material, which changes anisotropy of magnetization and magnetic permeability in the magnetic material. That is, these are directly related to a life of the structural material or power consumption of a motor, and control of the strain and measurement thereof are extremely important for the above-mentioned material development. On the other hand, however, quantitative measurement of the strain or evaluation of its distribution state is not easy.

At present, there is a method (KAM method: kernel average misorientation method) of measuring a change of a lattice constant and an azimuth difference by electron back scattered diffraction (EBSD), but a strain amount of about 0.01% is a detection limit at present. Further, many iron and steel materials have magnetism because a main component is iron, and in particular, attempts have also been made to obtain information relating to the strain by observing a magnetic domain in an electromagnetic steel plate and the like.

Since a size and a shape of the magnetic domain change depending on the strain, the strain is evaluated by a Kerr effect microscope which is a magnetic domain observation device using an optical microscope. However, in the method, quantitative evaluation of the strain is difficult, and a tendency of the strain in a wide field of view can be determined. As performances of the steel material and the magnet material improve, more detailed evaluation of the strain in the materials has become necessary and a highly accurate detection method is required.

Therefore, a device that can analyze the strain in the iron and steel material and the magnet material and present the distribution thereof or the strain amount, or an analysis method thereof is desired.

Solution to Problem

An aspect of the present disclosure provides a scanning electron microscope including a spin detector configured to measure spin polarization of a secondary electron emitted from a sample, and an analysis device configured to analyze measurement data of the spin detector, in which the analysis device determines a width of a region where the secondary electron spin polarization locally changes in the measurement data, and evaluates a strain in the sample based on the width of the region.

Advantageous Effect

According to one aspect of the present disclosure, it is possible to analyze the strain in a magnetic material with high accuracy.

BRIEF DESCRIPTION OF DRAWINGS

FIG. 1A is a schematic diagram of a scanning electron microscope having a function of detecting spin polarization of secondary electrons.

FIG. 1B shows a configuration example of a calculation display device of the scanning electron microscope.

FIG. 2A shows a secondary electron spin polarization mapping image of a strained permalloy and a domain wall width measurement result.

FIG. 2B shows a secondary electron spin polarization mapping image of a strain-free permalloy and a domain wall width measurement result.

FIG. 3 shows an example of a secondary electron spin image acquisition and analysis screen in a scanning electron microscope control device.

FIG. 4A shows a measured value of magnetization in an example of domain wall width analysis.

FIG. 4B shows a line obtained by fitting the measured value of the magnetization shown in FIG. 4A with a trigonometric function.

FIG. 4C shows a line obtained by fitting a value obtained by differentiating the measured value of the magnetization shown in FIG. 4A with an approximate function.

FIG. 5A shows an example of a direction where analysis is performed at a detected domain wall position in the example of domain wall width analysis.

FIG. 5B shows an analysis result in the direction shown in FIG. 5A.

FIG. 6A shows a magnetization component image in an example of strain distribution analysis.

FIG. 6B shows an image obtained by connecting portions having the same domain wall width in the magnetization component image of FIG. 6A.

FIG. 6C shows a strain distribution image generated from the image of FIG. 6B.

FIG. 7 shows an example of a secondary electron spin image analysis screen in the scanning electron microscope control device.

FIG. 8A shows a magnetization component image in an example of quantitative analysis of a strain in a sample.

FIG. 8B shows an example of a domain wall analysis result of the magnetization component image of FIG. 8A.

FIG. 9 shows an example of analysis considering a variation in a material type, crystallinity, and crystal orientation within a field of view.

DESCRIPTION OF EMBODIMENTS

FIG. 1A shows a basic configuration of an electron microscope of the present disclosure. The electron microscope is a strain measuring device that performs strain measurement of a magnetic body. The electron microscope includes a stage that fixes a sample 101, an electron optical system that scans the sample while emitting a focused primary electron beam 104, a spin detector 103 that measures spin polarization of secondary electrons 102 emitted from the sample, and a calculation display device 100.

FIG. 1B shows a configuration example of the calculation display device 100. The calculation display device 100 is an analysis device and can be constituted by a general computer and peripheral devices thereof. The calculation display device 100 is a computer system that executes a program for analyzing secondary electron spin polarization data. The calculation display device 100 includes a processor 110, a main storage device 120, an auxiliary storage device 130, and an interface (I/F) 140. These are connected to an internal bus and can communicate with each other.

The calculation display device 100 further includes a display device 150 and an input device 162. These are connected to the internal bus via the I/F 140. The display device 150 is an output device, and is, for example, an LCD display or a projector. The input device is, for example, a touch input device, a pen input device, a mouse, or a combination of all or a part thereof.

The processor 110 implements a predetermined function of the calculation display device 100 by operating according to a program stored in the main storage device 120. The main storage device 120 is, for example, a volatile storage device, and stores the program executed by the processor 110 and reference data. For example, the main storage device 120 stores an analysis program 121 in addition to an operating system. The processor 110 analyzes magnetization and a strain of the sample according to the analysis program 121 as to be described later.

The auxiliary storage device 130 is, for example, a non-volatile storage device, and stores data loaded in the main storage device 120. In the example of FIG. 1B, the auxiliary storage device 130 stores a database 131. The database 131 shows a relationship between a domain wall width and a strain amount as to be described later. The main storage device 120, the auxiliary storage device 130, and a combination thereof are storage devices. The configuration shown in FIG. 1B is an example, and the calculation display device 100 may have components connected via a network and may include a plurality of computers.

The calculation display device 100 analyzes the secondary electron spin polarization data and displays the data in accordance with a scanning signal of a primary electron beam. In FIG. 1A, the calculation display device 100 displays a mapping image 107 of secondary electron spin polarization (magnetization) taken by a scanning electron microscope. The mapping image 107 includes a magnetic domain 105 and a domain wall 106.

In FIG. 1A, only one magnetic domain and one domain wall are designated by reference numerals 105 and 106, respectively. The magnetic domain 105 is a region where the magnetization is constant. The domain wall 106 is a boundary region between magnetic domains, where a magnetization direction (secondary electron spin polarization) largely changes locally. The calculation display device 100 has a function of deriving the domain wall width of the domain wall extracted from the mapping image 107. The calculation display device 100 performs visualization of strain distribution of the sample and/or quantitative evaluation of the strain based on the domain wall width.

The secondary electron spin polarization, which is an input signal of the scanning electron microscope for mapping the secondary electron spin polarization of the present disclosure, is a physical quantity that reflects the magnetization of the sample. The region where the magnetization is uniform is the magnetic domain, and a region where the magnetization locally rotates is the domain wall. It is known that the width of the domain wall has the following relationship with a magnitude (K) of magnetic anisotropy that determines a direction of easy magnetization in the material.

$$d \propto 1/\sqrt{K} \quad \text{[Formula 1]}$$

When the strain occurs in the sample and a change in an interatomic interval occurs, the magnetic anisotropy changes at that portion. It is known that the magnetic anisotropy thereof largely changes even at a strain of $10^{-6}$ level. Therefore, when the strain occurs, the magnetic anisotropy and the width of the domain wall in the portion change. In a case of an iron and steel material, the width of the domain wall is in a range of several ten nm to several hundred nm, which is a range measurable by the scanning electron microscope. Therefore, in a secondary electron spin polarization mapping image, the strain in the sample can be evaluated by displaying a region (domain wall) where the secondary electron spin polarization (magnetization) locally changes and evaluating a region width (domain wall width).

FIGS. 2A and 2B show an example of measurement of differences in the domain wall width due to presence or absence of strain. FIG. 2A shows a secondary electron spin polarization mapping image 21A of a strained permalloy and a magnetization change 22A caused by a position. FIG. 2B shows a secondary electron spin polarization mapping image 21B of a strain-free permalloy and a magnetization change 22B caused by the position. It can be seen from comparison of FIGS. 2A and 2B that the differences in the domain wall width due to the presence or absence of the strain can be measured.

In order to perform measurements shown in FIGS. 2A and 2B, two pieces of sample permalloy were prepared, and one of them was annealed, and removed of strains. Thereafter, a strain was generated by locally applying stress to one of the two pieces of sample permalloy. The scanning electron microscope measured the secondary electron spin polarization of the stressed sample (strained) and the unstressed sample (strain-free) and formed respective mapping images.

The secondary electron spin polarization mapping images (electron micrographs) 21A and 21B in FIGS. 2A and 2B show magnitudes of the secondary electron spin polarization (magnetization) in a gray scale. White and black regions with uniform contrast show the magnetic domain, and a boundary portion shows the magnetic domain wall. In FIGS. 2A and 2B, a result of analyzing a change in the magnetization in a direction perpendicular to the domain wall (shown by a white line) is shown in the graphs 22A and 22B on a right side of the mapping images 21A and 21B, respectively.

In the graphs 22A and 22B, a horizontal axis shows a position on a sample surface and a vertical axis shows the magnitude of the magnetization. A portion where the magnetization changes rapidly corresponds to the boundary portion of the black and white regions of the spin polarization mapping image and is the domain wall. The width of the domain wall, that is, the width of the region where the magnetization changes is 260 nm in the strained sample, and is 480 nm in the strain-free sample. In this way, it can be seen that the width of the domain wall changes depending on the presence or absence of the strain, and the change can be measured by the scanning electron microscope that detects the secondary electron spin polarization.

According to one aspect of the present disclosure, first, the magnetization of the sample is mapped by the secondary electron spin polarization, and the portion (domain wall) where the magnetization largely changes is extracted. The domain wall may be selected by a user from the input device 162, or may be automatically extracted by the processor 110 which operates according to the analysis program 121. The domain wall to be measured can be accurately specified by the user input. The automatic extraction does not require the user input.

The secondary electron spin polarization of the sample is acquired as digital data, and shows the secondary electron spin polarization of a plurality of directional components in each of two-dimensionally arrayed pixels. For example, the secondary electron spin polarization data shows spin polarization components (magnetization components) in an X direction, a Y direction, and a Z direction orthogonal to each other in each pixel of 512 pixels×512 pixels arranged in a matrix. The secondary electron spin polarization component in a specific direction shows a magnitude and a direction, and shows a positive or negative value depending on the direction.

In a configuration in which the calculation display device 100 automatically extracts the domain wall, the calculation display device 100 subtracts a background from acquired measurement data of the secondary electron spin polarization, and then identifies the domain wall based on the positional change of the spin polarization. For example, the calculation display device 100 detects a portion where the secondary electron spin polarization component in the specific direction changes largely by more than a predetermined value between two points at a predetermined distance, and determines that the domain wall exists at the detected portion (between the two points). The calculation display device 100 may use an average value of changes in the secondary electron spin polarization components in the three directions.

The specific direction is, for example, a direction where a difference between a maximum value and a minimum value of the secondary electron pin polarization in the X direction, the Y direction, and the Z direction is maximum. Alternatively, the magnetization direction determined from the components in the three directions may be used as the specific direction. The predetermined distance is, for example, 1 µm. The predetermined value is, for example, a value that is 50% of the difference between the maximum value and the minimum value of the spin polarization in a field of view. As described above, the spin polarization shows the direction depending on whether the direction is positive or negative.

The above-mentioned predetermined distance is set to a value larger than the domain wall width. As described above, the domain wall width is several ten nm to several hundred nm, and 1 µm can identify the two points of the magnetic domain that sandwiches the domain wall. The above-mentioned predetermined value is preset considering an influence of noise of the input signal. A value that can detect the change in the secondary electron spin polarization component in the domain wall is selected regardless of a fluctuation in a measured value caused by the noise.

The domain wall can be detected by a method different from the above-mentioned method. For example, the calculation display device 100 maps an absolute value of the above-mentioned directional component of the magnetization by squaring a value of each pixel of a certain magnetization component image and mapping a square root thereof. The calculation display device 100 identifies the domain wall based on a change (difference) in the absolute value in an absolute value mapping image.

The magnetization rotates in the domain wall, and the magnetization direction in the domain wall differs from the magnetization direction in the magnetic domain. Therefore, the absolute value of the above-mentioned directional component of the magnetization in the magnetic domain differs from the absolute value of the directional component of the magnetization in the domain wall. Further, the absolute value of the above-mentioned directional component of the magnetization in the magnetic domain is constant, and the absolute value of the directional component of the magnetization in the domain wall changes.

Therefore, the absolute value mapping image shows different values in the domain wall and the magnetic domain. Further, the absolute value mapping image shows the absolute value that changes in the domain wall and the constant absolute value in the magnetic domain. For example, in the absolute value mapping image, the calculation display device 100 specifies a region where the absolute value is constant as the magnetic domain, and determines a region (position) showing an absolute value different from the magnetic domain between the magnetic domains as the domain wall (position thereof).

The calculation display device 100 determines the width of the domain wall after specifying the position of the domain wall as described above. A width of a magnetization transition region in a direction perpendicular to the direction where the domain wall extends matches the domain wall width. Therefore, it is necessary to identify the direction where the domain wall extends. In one example, the user uses the input device 162 to input the direction where the domain wall extends.

For example, the user can indicate the direction where the domain wall extends by tracing the domain wall with a pointer in the spin polarization mapping image or the absolute value mapping image. The direction where the domain wall extends may be constant or variable. Alternatively, the user may select a plurality of points on the domain wall in the mapping image and input the direction of the domain wall width at each of the selected points.

In another example, the processor 110 which operates according to the analysis program 121 may automatically detect the direction of the domain wall. For example, the calculation display device 100 selects one point on the domain wall depending on the user input or automatically, and measures the width of the region where the magnetization changes at the point in a plurality of directions. When a vertical direction of the mapping image is 0 degree, for example, the calculation display device 100 measures the width in 20 directions at an interval of 18 degrees. A direction showing a minimum value in the measured values is the direction of the domain wall width, which is the direction perpendicular to the direction where the domain wall extends.

When the direction of the domain wall width is identified, the calculation display device 100 measures a length of a magnetization change in the direction as the domain wall width. In the method of measuring the domain wall width, for example, a half value width of a peak waveform derived from a parameter obtained by fitting an arctangent function to the measurement data of the magnetization change, or derived by differentiating a value of the magnetization in a measurement direction, is determined as the domain wall width. The width can be accurately determined by fitting the function.

The calculation display device 100 stores correlation data showing a relationship between the domain wall width and the strain or the stress in a standard sample. The calculation display device 100 can quantitatively estimate the strain or the stress in the material by comparing the measured domain wall width with pre-registered correlation data. It should be noted that the stress represents the strain.

For example, in a case of an iron material, basically a so-called 180-degree domain wall, in which the magnetization in the magnetic domain and the domain wall are parallel, occupies most. In this case, no magnetic pole is generated on the domain wall and a magnetic domain structure is stable. However, the strain which occurs in the sample locally complicates an easy magnetization direction. As a result, the domain wall is not parallel to the magnetization in the magnetic domain, and the magnetic pole may be generated on the domain wall.

In such a case, the calculation display device 100 evaluates the strain amount including not only the domain wall width but also a relative angle between the magnetization and the domain wall. For example, the calculation display device 100 corrects the domain wall width with a preset equation based on the angle between the direction of the magnetization and the direction where the domain wall extends. The angle is, for example, an average value of angles (no direction) of magnetic domains that sandwich the domain wall or one of the values. As an example, the domain wall width is corrected with a cosine function of the relative angle.

Further, in a case of a polycrystalline sample, when orientations of crystal grains are different, an influence of strain on the domain wall width is different. In this case, in order to evaluate the strain distribution in the entire field of view, it is necessary to consider discontinuity of the domain wall width at a crystal grain boundary portion. Therefore, the calculation display device 100 specifies a boundary portion position of each crystal grain by, for example, an electron back scattered diffraction (EBSD) or a secondary electron image.

Alternatively, there is also a method of estimating the crystal grain boundary portion position from the magnetization direction in the magnetic domain by utilizing a property that an axis of easy magnetization (easy magnetization axis) is parallel to a crystal axis of the material in many magnetic materials. Since a slight deviation in a crystal axis direction occurs between different adjacent particles, the magnetization direction also shifts accordingly.

In a case of a cubic iron-based material, the easy magnetization axes are three axes including (100), (010), and (001) which are orthogonal to each other. When the magnetization direction in adjacent magnetic domains are 180 degrees or 90 degrees, the magnetic domain is in the same crystal grain, and in a case of other angles, the magnetic domain exists over separate crystal grains, and the crystal grain boundary portion exists between the crystal grains.

Therefore, the calculation display device 100 can specify the position of the crystal grain boundary portion by analyzing the magnetization direction. The method of identifying the crystal grain boundary portion from the magnetization direction is used in the case of the material whose magnetization is oriented to the easy magnetization axis, and in a case of a material whose strain is large, the magnetization may not be oriented to the easy magnetization axis. Therefore, the calculation display device 100 performs the analysis considering this point.

After grasping the crystal grain boundary portion position with the method as described above, the calculation display device 100 measures the domain wall width, evaluates the strain distribution in each crystal grain using the above-mentioned method, and then connects the strain amount between the crystal grains. Since the boundary portion is a place where a composition and the crystallinity are unique, it is necessary to be careful in comparison with other regions.

The present embodiment discloses a scanning electron microscope that derives the strain amount or the strain distribution based on the result of the domain wall width measurement, or an analysis method thereof. Various aspects are contemplated and several examples are shown below.

First Embodiment

FIG. 3 shows an example of an analysis screen in the scanning electron microscope that detects the secondary electron spin polarization and that is equipped with the function of the present disclosure. The user can use the input device 162 to specify a process to be executed by the calculation display device 100 from a menu bar 300. For example, when "data analysis" is selected, the calculation display device 100 displays an analysis menu 350. The calculation display device 100 performs an analysis process selected in the analysis menu 350.

For example, in a secondary electron spin polarization image acquisition mode, the calculation display device 100 forms and displays a surface topography image 310 by plotting the total number of detected secondary electrons. Further, the calculation display device 100 generates and displays a magnetization component image 320 based on spin polarization data from a spin detector 3. It is known that the spin polarization of secondary electrons has a correlation with the magnitude of the magnetization. The calculation display device 100 can acquire component images in each magnetization direction, for example, component images in the X direction, Y direction, and Z direction. In the example of FIG. 3, the calculation display device 100 displays only the magnetization component image 320 of one magnetization component (for example, a component with a largest magnetization change).

As described above, the calculation display device 100 specifies a position of a magnetic domain 302 which is the region where the magnetization is constant and a position of a domain wall 303 where the magnetization rapidly changes in the magnetization component image 320. In FIG. 3, only one magnetic domain and only one domain wall are designated by reference numerals 302 and 303, respectively as an example.

As described above, the calculation display device 100 examines a change in data in a specific direction (for example, vertical or horizontal direction) in acquired two-dimensional array data, for example, automatically detects a portion where the magnetization largely changes by more than a predetermined value in a region within 1 micron, and determines the portion as the domain wall. A predetermined amount of change is, for example, 50% of a difference between a maximum value and a minimum value of the magnetization in a field of view. The calculation display device 100 may perform a process such as data averaging (smoothing) as necessary to ensure S/N.

Instead of the calculation display device 100 automatically specifying the position of the magnetic domain 302 and the position of the domain wall 303, the calculation display device 100 may specify the position of the magnetic domain 302 and the position of the domain wall 303 according to the designation from the input device 162 by the user.

The calculation display device 100 squares data of the magnetization component image 320 and maps a square root thereof to generate and display an absolute value mapping image 330. In the magnetization component image 320, regions (magnetic domains) of the magnetization (for example, the magnetizations 304 and 305) which are antiparallel to each other have the same absolute value of the magnetization. Therefore, values of these regions in the absolute value mapping image 330 are the same.

On the other hand, the magnetization rotates in the domain wall, and the magnetization direction in the domain wall is different from the magnetization direction in the magnetic domain. Therefore, in the absolute value mapping image 330, the domain wall and an inside of the magnetic domain show different values. The calculation display device 100 can identify the domain wall position by analyzing the absolute value mapping image 330. The calculation display device 100 specifies the domain wall position, analyzes a width thereof, and displays a domain wall width analysis graph 340 showing a result thereof.

FIGS. 4A, 4B and 4C show examples of a method for measuring the domain wall width. The calculation display device 100 estimates the domain wall width after specifying the domain wall position. As shown in FIG. 4A, the calculation display device 100 creates a graph showing a relationship between a measured value 400 of the magnetization in the vicinity of the domain wall and a position. As shown in FIG. 4B, the calculation display device 100 further performs curve fitting on the measured value 400 using an approximate function 401, for example, arc tangent.

When a horizontal axis (x) is a position in the field of view, a vertical axis (y) is the magnitude of the magnetization, an origin of x is the domain wall position, and an origin of y is a reference point of the magnetization (an intermediate value of values of the magnetization in the magnetic domains on both sides of the domain wall), the following equation is given.

$$y = b * \arctan(x/a) \quad \text{[Formula 2]}$$

a is a parameter related to the domain wall width, and for example, an optimum value of the above-mentioned a can be obtained by comparing a with data acquired with a least square method.

In another example, as shown in FIG. 4C, the calculation display device 100 may perform the curve fitting using an approximate function 402 on a graph showing a relationship between a differential value obtained by the position of the measured value of the magnetization and the position. In this case, the calculation display device 100 can determine the domain wall width by evaluating a width of a peak waveform.

The domain wall width obtained as described above may differ depending on a direction to be measured. That is, the obtained results differ depending on taking the horizontal axis (x) shown in FIGS. 4A, 4B, and 4C in which direction.

FIG. 5A shows four directions A to D where the value of the magnetization is measured in a secondary electron spin polarization mapping image in order to determine the domain wall width after specifying a position of a domain wall 500. The calculation display device 100 plots and compares values of the magnetization in the four directions A to D. Graphs 510A to 510D in FIG. 5B show changes in the magnetization in the four directions A to D, respectively.

The calculation display device 100 performs analysis in a plurality of directions as described with reference to FIGS. 4A, 4B, and 4C, and determines a minimum value as the domain wall width at that position. When the number of directions to be measured is set to, for example, 20 or 40, accuracy can be further improved. Basically, when measurement is performed in a direction perpendicular to a direction where the domain wall extends, the domain wall width is measured narrowest.

Unlike the above-mentioned example, the user may specify the direction where the domain wall extends from the input device 162. The calculation display device 100 may identify the direction where the domain wall extends by sequentially detecting the domain wall position, and perform the domain wall width analysis described with reference to FIGS. 4A, 4B, and 4C in the direction perpendicular to the direction.

Second Embodiment

Another example of strain analysis will be described with reference to FIGS. 6A to 6C. Herein, an example of deriving a strain distribution after measuring the domain wall width is shown. FIG. 6A shows a schematic diagram of a secondary electron spin polarization mapping image (magnetization component image) 60A in a strained magnetic body sample. A magnetic domain 600 and a domain wall 601 are shown, and the domain wall width differs depending on a magnitude of the strain at each place.

FIG. 6B shows an image 60B obtained by connecting portions having the same domain wall width in the magnetic domain image 60A (same field of view) of FIG. 6A. The calculation display device 100 measures the domain wall width at a plurality of portions, and forms and displays a line obtained by connecting the portions having the same domain wall width. A line formed by connecting points having the same domain wall width is a line obtained by connecting points having the same strain amount. In FIG. 6B, two lines 603 and 604 are shown. The line 603 is a line obtained by connecting portions having the small domain wall width, and the line 603 is a line obtained by connecting portions having the small domain wall width. A strain of the portions shown by the line 603 is small, and a strain of the portions shown by the line 604 is large.

FIG. 6C shows a strain distribution image 60C generated from the image 60B shown in FIG. 6B. The strain distribution image 60C shows a tendency of a magnitude of the strain amount in the field of view. In the example of FIG. 6C, the region within the field of view is classified into a region 605 having a large strain, a region 606 having an average strain amount, and a region 607 having a small strain.

The calculation display device 100 identifies the three regions 605, 606, and 607 divided by the lines 603 and 604 in the image shown in FIG. 6B, and gives a different pattern to each region to generate the strain distribution image 60C.

FIG. 7 shows an example of a secondary electron spin image analysis screen of the calculation display device 100 of the scanning electron microscope using a function of visualizing the strain distribution. When the secondary electron spin polarization is detected, the calculation display device 100 forms a topography image 710 of a sample surface by counting the number of secondary electrons that enter the detector 3. The calculation display device 100 displays the topography image 710.

The calculation display device 100 generates and displays a magnetization component image 720 based on spin polarization data from the spin detector 3. Although three magnetization component images can be generated at maximum (two components in a sample surface and a perpendicular component), only one magnetization component image 720 is displayed here.

Herein, a case where there is a defect 701 causing the strain on the surface of the sample and the strain is large in the vicinity of the defect will be described. In the magnetization component image 720, a position and a shape of a magnetic domain 702 and a position and a shape of a domain wall 703 are visualized, and a magnetization vector 704 can also be derived. The calculation display device 100 measures the domain wall width and displays an image 730 obtained by connecting portions having the same domain wall width. A curve 705 obtained by connecting portions having a large domain wall width and a curve 706 obtained by connecting portions having a small domain wall width are displayed. The calculation display device 100 selects, for example, a domain wall width having a preset difference, and generates a line obtained by connecting portions having the respective domain wall widths.

Further, the calculation display device 100 generates and displays a strain distribution image 740 based on the image 730. The strain distribution image 740 represents the strain amount in shades, and displays a region 708 with the large strain in the vicinity of the defect and a region 707 with a small strain distant from the defect. In order to generate the images 710 to 740, for example, a user selects an item of "data analysis" on a menu bar 700 and further selects an item of "domain wall width analysis" within the item. The calculation display device 100 analyzes the domain wall width according to the above-described procedure according to the user input, and displays a result thereof.

Third Embodiment

FIGS. 8A and 8B show another example of strain analysis. FIG. 8A shows a magnetization component image. As shown in FIG. 8A, the calculation display device 100 specifies a magnetic domain 800, a domain wall 801, and a magnetization vector 802 in the magnetization component image in which the secondary electron spin polarization is mapped.

The calculation display device 100 numbers each point along the domain wall, evaluates the domain wall width at the point, and evaluates the strain amount based on information on a material type and a magnetization direction. FIG. 8B shows a table 820 of a domain wall analysis result. In the example of FIG. 8B, the domain wall width, an angle between the domain wall and the magnetization, and the strain amount at each point are shown. The calculation display device 100 displays the table 820 of the domain wall analysis result as the analysis result. The table 820 shows information of the strain distribution in a sample.

The domain wall width and a magnetization rotation angle are specified by analyzing the magnetization component image as described above. The angle between the domain wall and the magnetization is an average value of an angle between a magnetization direction of two magnetic domains that sandwich the domain wall and a direction where the domain wall extends, or an angle between one magnetization direction and the direction where the domain wall extends. It should be noted that no direction is defined for the angle between the magnetization direction and the domain wall.

Since the domain wall width is related to the strain amount through the magnetic anisotropy, the calculation display device 100 can quantitatively derive the strain by comparing the domain wall width with the database 131 prepared in advance. The database 131 shows a relationship between the domain wall width and the strain amount (for example, represented by a stress) for each material. As described above, in order to derive the strain amount, the domain wall width is corrected by the angle between the magnetization direction and the domain wall.

In a case of a soft magnetic body sample such as an iron material, the magnetization is mainly on a so-called 180-degree domain wall, which is reversed on both sides of the domain wall. The magnetization is parallel to the domain wall, and it is stable when no magnetic pole occurs on the domain wall. However, when the magnetic anisotropy occurs due to the strain, the above-mentioned state may not be obtained. Including that, the calculation display device 100 also analyzes the magnetization directions on both sides of the domain wall, and a case of unique magnetization is excluded from a normal analysis method. Further, information such as an average value and dispersion of the domain wall width is also important for evaluation of material properties, and are accordingly included in the analysis items.

Fourth Embodiment

FIG. 9 shows another example of strain analysis. An enlarged view 960 is an enlarged view of a region surrounded by a rectangle in a field of view 950. When there is a difference in a material type, crystallinity, and crystal orientation of a sample within the field of view 950, a relationship between the strain amount and the domain wall width may become discontinuous at a boundary portion (grain boundary portion) 903 thereof. This corresponds to a polycrystalline sample. In this case, a boundary portion needs to be derived in advance from a scanning electron microscope image or the like, and it is necessary to analyze the boundary portion in consideration of discontinuity in the portion.

For example, in the enlarged view 960, domain walls 906 and 907 are discontinuous with the grain boundary portion 903 sandwiched between a crystal grain 904 existing above and a crystal grain 905 existing below. The calculation display device 100 first evaluates the strain distribution and the strain amount in each grain, and then connects points of the same strain amount among the crystal grains. Further, since the grain boundary portion 903 itself is a place where a composition and the crystallinity are unique, it is necessary to be careful in comparison with other regions in the domain wall width evaluation and the strain analysis at the point.

The calculation display device 100 may form a strain distribution image extending over different crystal grains from the domain wall width without determining the strain amount. For example, the calculation display device 100 specifies a continuous domain wall extending over the different crystal grains and matches the domain wall width of one crystal grain with the domain wall width of another crystal grain. A coefficient also acts on the domain wall width of the other crystal grain. Thereafter, the calculation display device 100 connects the positions having the same domain wall width in these crystal grains to form the strain distribution image.

The invention is not limited to the above-mentioned embodiments, and includes various modifications. For example, the embodiments described above are described in detail for easy understanding of the invention, and the invention is not necessarily limited to those including all the configurations described above. Further, a part of the configuration of one embodiment can be replaced with the configuration of another embodiment, and the configuration of another embodiment can be added to the configuration of one embodiment. Further, a part of the configuration of each embodiment may be added to, deleted from, or replaced with another configuration.

Further, each of the above-mentioned configurations, functions, process units, and the like may be partially or entirely implemented by hardware such as through design using an integrated circuit. Further, the above-mentioned configurations, functions, and the like may be implemented by software by means of a processor interpreting and executing a program for implementing corresponding functions. Information of programs, tables, files or the like for implementing each function can be placed in a recording device such as a memory, a hard disk, and a solid state drive (SSD), or a recording medium such as an IC card or an SD card.

Further, control lines and information lines show those considered to be necessary for the description, and not all the control lines and the information lines are necessarily shown on the product. In practice, it may be considered that almost all the configurations are connected to each other.

The invention claimed is:

1. A scanning electron microscope comprising:
   a spin detector configured to measure spin polarization of a secondary electron emitted from a sample; and
   an analysis device configured to analyze measurement data of the spin detector, wherein
   the analysis device is configured to
      determine a width of a region where the secondary electron spin polarization locally changes in the measurement data, and
      evaluate a strain in the sample based on the width of the region.

2. The scanning electron microscope according to claim 1, wherein
   the analysis device is configured to detect a position where the secondary electron spin polarization locally changes in the measurement data.

3. The scanning electron microscope according to claim 1, wherein
   the analysis device is configured to determine a width of a region which is specified by a user and where the secondary electron spin polarization locally changes.

4. The scanning electron microscope according to claim 1, wherein
   the analysis device is configured to:
      determine a width of a region where the secondary electron spin polarization changes in a plurality of directions in a position where the secondary electron spin polarization locally changes, and
      evaluate the strain in the sample based on a minimum value of the width.

5. The scanning electron microscope according to claim 1, wherein
   the analysis device is configured to:
      determine the width of the region where the secondary electron spin polarization changes by fitting an approximate function.

6. The scanning electron microscope according to claim 1, wherein
   the analysis device is configured to:
      determine a magnitude of the strain in the sample based on a magnitude of the width of the region where the secondary electron spin polarization locally changes, and
      determine a strain distribution in the sample based on the magnitude of the strain and display information indicating the strain distribution.

7. The scanning electron microscope according to claim 1, wherein
   the analysis device is configured to:
      evaluate the strain in the sample based on the width of the region where the secondary electron spin polarization locally changes and a direction of spin polarization in a region adjacent to the region.

8. The scanning electron microscope according to claim 1, wherein
   the analysis device is configured to:
      store a database that associates the width of the region where the secondary electron spin polarization locally changes with a strain amount, and
      determine the strain amount by comparing the width of the region where the secondary electron spin polarization locally changes and which is determined in the measurement data and the database.

9. The scanning electron microscope according to claim 1, wherein
   the analysis device is configured to:
      specify a plurality of crystal grains in the sample,
      evaluate a strain in each of the plurality of crystal grains, and
      determine a strain distribution in the sample by connecting an evaluation result of the strain in each of the plurality of crystal grains.

10. A method of analyzing secondary electron spin polarization of a sample measured with a scanning electron microscope by an analysis device, the method comprising:
    determining, by the analysis device, a width of a region where the secondary electron spin polarization locally changes in measurement data of the secondary electron spin polarization; and
    evaluating, by the analysis device, a strain in the sample based on the width of the region.

11. The method according to claim 10, further comprising:
    specifying, by the analysis device, a position where the secondary electron spin polarization locally changes in the measurement data.

12. The method according to claim 10, further comprising:
    determining, by the analysis device, the width of the region where the secondary electron spin polarization locally changes and which is specified by a user.

13. The method according to claim 10, further comprising:

determining, by the analysis device, a width of a region where the secondary electron spin polarization changes in a plurality of directions in a position where the secondary electron spin polarization locally changes; and evaluating, by the analysis device, the strain in the sample based on a minimum value of the width.

14. The method according to claim 10, further comprising:

determining, by the analysis device, the width of the region where the secondary electron spin polarization changes by fitting an approximate function.

15. The method according to claim 10, further comprising:

determining, by the analysis device, a magnitude of the strain in the sample based on a magnitude of the width of the region where the secondary electron spin polarization locally changes; and determining, by the analysis device, a strain distribution in the sample based on the magnitude of the strain, and displaying information indicating the strain distribution.

* * * * *